United States Patent
Treants

[19]

[11] Patent Number: 6,029,650
[45] Date of Patent: Feb. 29, 2000

[54] PERSONAL HEATING DEVICE

[76] Inventor: Bill Treants, 5230 S. Skyline Dr., New Berlin, Wis. 53151

[21] Appl. No.: 09/265,475

[22] Filed: Mar. 10, 1999

[51] Int. Cl.[7] ............................... F24C 1/16; A61F 7/00; F23D 3/16

[52] U.S. Cl. ............................ 126/204; 126/58; 126/59; 126/45; 126/4; 126/38; 126/9 R; 431/291

[58] Field of Search ................................. 126/58, 59, 9 R, 126/65, 261, 79, 262, 291, 56, 57, 4, 45, 38, 46, 47, 204, 205, 206, 208; 362/161, 162, 180, 163, 447; 431/289, 291

[56] References Cited

U.S. PATENT DOCUMENTS

| | | |
|---|---|---|
| 1,739,138 | 12/1929 | Giragosian . |
| 2,567,323 | 9/1951 | Cyphert . |
| 2,678,644 | 5/1954 | Banks et al. ............................... 126/43 |
| 2,771,763 | 11/1956 | Kracauer ................................. 431/291 |
| 3,110,301 | 11/1963 | Bricker . |
| 3,144,015 | 8/1964 | Jankowski .............................. 126/261 |
| 3,420,221 | 1/1969 | Wintz . |
| 4,186,430 | 1/1980 | Britton ................................... 362/162 |
| 4,241,721 | 12/1980 | Holly ...................................... 126/204 |
| 4,676,223 | 6/1987 | Peterson ................................. 126/208 |
| 5,197,454 | 3/1993 | Lee .......................................... 126/45 |

*Primary Examiner*—Carl D. Price
*Attorney, Agent, or Firm*—Quarles & Brady LLP

[57] ABSTRACT

A personal heating device includes a chamber having a closed end and an opposing open end. One or more air intake holes are formed in the chamber proximal the closed end to allow air into the chamber. One or more vent holes are formed proximal the opposing open end to allow air to exit the chamber. A heat source disposed inside the chamber holds generates heat, and a cap slidably covers the chamber open end to hold in the heat and regulate the air exiting the vent holes.

14 Claims, 1 Drawing Sheet

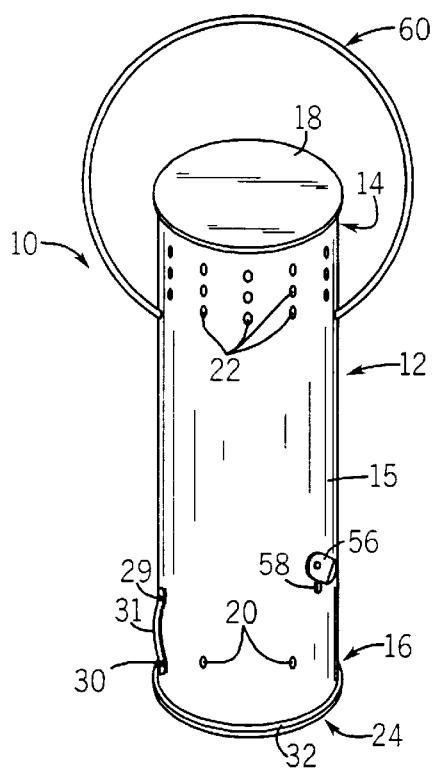
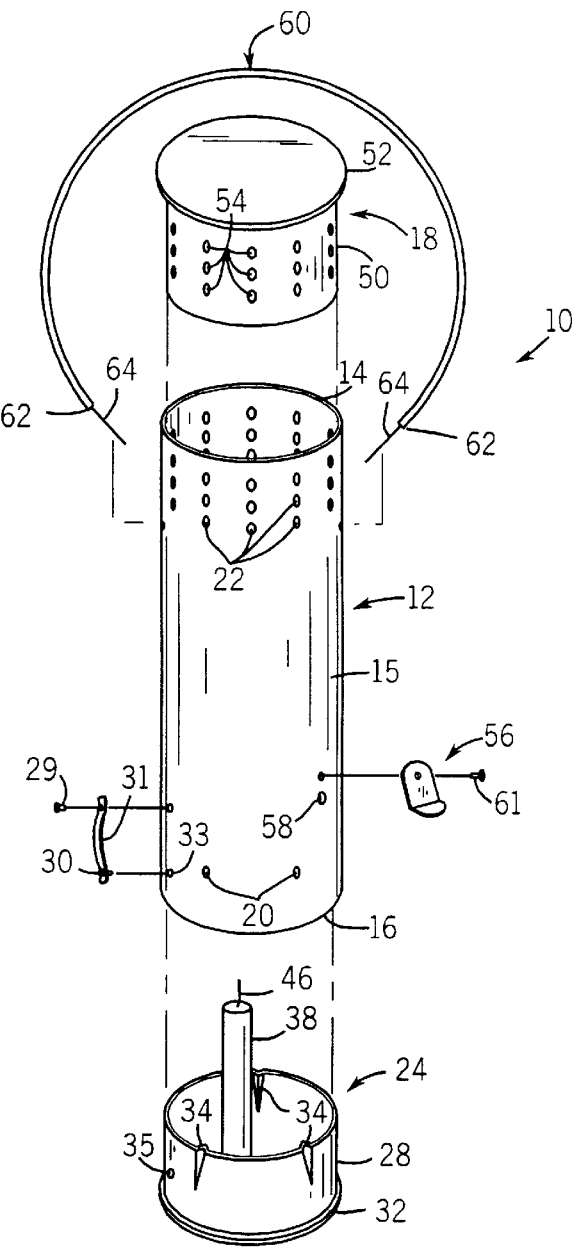
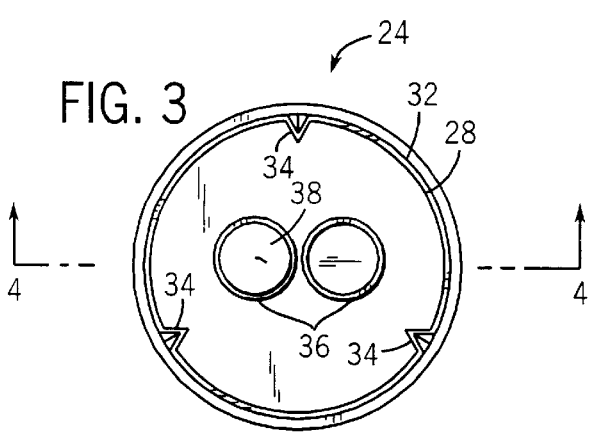
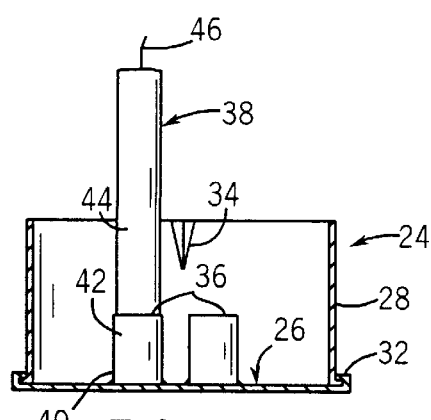

PERSONAL HEATING DEVICE

BACKGROUND OF THE INVENTION

The field of invention is heating devices, more particularly compact heating devices suitable for personal use.

Individuals located in cool climates often find occasion to venture outdoors when the air temperature is cooler than desired. These outdoor excursions may include planned activities, such as hunting or ice fishing, or may be unplanned, such as resulting from a stalled automobile. In any event, the individual may be exposed to cold temperatures for extended periods of times. While being exposed to these cold temperatures, it is extremely desirable for the individual to have a personal heating device which keeps the individual warm. Certain activities in the outdoors, also require a certain degree of mobility, such as walking or climbing a tree while hunting. Therefore a compact heating device is also desirable.

One particular personal heating device has an electrical heating element formed part of gloves, socks or boots, which is powered by a battery. These devices are compact, but require a generous supply of batteries to maintain the heat output for more than a few hours. Furthermore, only a portion of the individual's body benefits from the heat generated by the electrical device.

Other devices that generate heat to warm an individual, such as described in U.S. Pat. No. 4,676,223, which includes a burner disposed in a container, wherein the container includes a seat on which the user sits, are too bulky to transport over long distances, such as required during hunting. Therefore, a need exists for a compact personal heating deice capable of providing heat over an extended period.

BRIEF SUMMARY OF THE INVENTION

The present invention provides a personal heating device which includes a tubular chamber having a closed end and an opposing open end. One or more air intake holes are formed in the chamber proximal the closed end to allow air into the chamber. One or more vent holes are formed proximal the opposing open end to allow air to exit the chamber. A heat source disposed inside the chamber generates heat, and a cap slidably covers the chamber open end to hold in the heat and regulate the air exiting the vent holes.

A general objective of the present invention is to provide a personal heating device which is capable of generating heat over an extended period of time. This is accomplished by providing a personal heating device capable of sustaining a heat source for an extended period.

Another objective of the present invention is to provide a compact heating device which is compact. This objective is accomplished by providing a heating device having a lightweight elongated chamber which is easy to transport.

Still another objective of the present invention is to provide a heating device which allows the user to regulate the device heat output. This objective is accomplished by providing a heating device in which the user can regulate the air intake and vents to control heat temperature of the device.

The foregoing and other objects and advantages of the invention will appear from the following description. In the description, reference is made to the accompanying drawings which form a part hereof, and in which there is shown by way of illustration a preferred embodiment of the invention.

BRIEF DESCRIPTION OF THE DRAWINGS

FIG. 1 is perspective view of a personal heating device incorporating the present invention;

FIG. 2 is an exploded perspective view of the device of FIG. 1;

FIG. 3 is a sectional of the endcap of the device of FIG. 1; and

FIG. 4 is a sectional view along line 4—4 of the device of FIG. 3.

DETAILED DESCRIPTION OF THE PREFERRED EMBODIMENTS

Referring to FIGS. 1 and 2, a personal heating device 10 has an elongated tubular chamber 12 with a capped top end 14 and a closed bottom end 16. The ends 14, 16 are joined by chamber walls 15. A flame heat source, such as a candle 38, disposed inside the chamber 12 proximal the bottom end 16 heats the chamber walls 15 to warm a user. A cap 18 slidably inserted into the top end 14 controls air exiting the chamber 12, and thus the heat retained in the device 10.

The cylindrical chamber 12 radiates heat generated by the flame heat source, and provides protection for the user from the flame. Air inlet holes 20 formed in the chamber wall 15 proximal the chamber bottom end 16 allow air to enter the chamber 12 and feed the flame. Air vent holes 22 formed in the chamber wall 15 proximal the top end 14 allow air and combustion gases to exit the chamber 12. Preferably the chamber 12 is formed from a lightweight inflammable material, such as aluminum or the like, and is approximately nineteen inches long and $4\frac{1}{8}$ inches in diameter, to provide a lightweight and easy to carry article. Although a cylindrical chamber 12 is preferred due to ease of manufacturing, other tubular chamber shapes may be used, such as a square or the like, without departing from the scope of the present invention.

The chamber bottom end 16 is closed by inserting an endcap 24 therein. The endcap 24 has an inwardly directed surface 26 surrounded by a collar 28. Preferably, the endcap 24 is formed from galvanized steel which is easy to form and corrosion resistant. A rim 32 radially extends from the collar 28 and is substantially coplanar with the inwardly directed surface 26. The rim 32 abuts the chamber bottom end 16.

The collar 28 extends into the chamber 12, and conforms to the chamber interior shape to provide a loose form fit. Preferably, the endcap collar 28 overlaps one or more of the air inlet holes 20 to discourage the heat source flame from extending through the holes 20. If the collar 28 covers the air inlet holes 20, indents 34 formed in the collar 28 are aligned with the inlet holes 20 to upwardly direct air entering the chamber 12, and discourage the flame from following a direct path to the exterior of the chamber 12 through the air inlet holes 22.

Preferably, the endcap 24 is releasably retained in the chamber bottom end 16 by a pin 30. The pin 30 is mounted on an end of a flexible metal strip 31. The other end of the strip is secured to the chamber wall 15 using a fastener 29, such as pop rivets, screws, or the like. The pin 30 passes through an opening 33 formed in the chamber wall 15 and is received in a pin receptacle 35 formed in the endcap collar 28. To release the endcap 24 from the chamber 12, the pin 29 is pulled away from the chamber wall 15, allowing the endcap 24 to slip out of the chamber bottom end 16.

As shown in FIG. 3, a candle holder 36 mounted to the endcap inwardly directed surface 26 holds a lit candle 38 to provide a heat source inside the chamber 12. Preferably, the cylindrical candle holder 36 is formed from a metal strip, and has one end 40 soldered to the cap surface 26, and the other end 42 is open for receiving the candle 38. Most preferably, the candle holder 36 is formed from a ductile metal strip, such as copper, which is easily deformable to retain the candle 38 therein. Other candle holders known in the art, such as a spike which impales the candle 38, may be used without departing from the scope of the present invention.

In the preferred embodiment, a plurality of candle holders 36 are mounted to the endcap surface 26. By providing a heating device with a plurality of candle holder, the heating device 10 is capable of receiving a like number of candles 38 to increase the device heat output.

The candle 38 has a base 44 inserted into the candle holder open end 42 and a wick 46 which is ignited to generate heat. In the preferred embodiment, the candle 38 is formed from non-toxic materials known in the art, approximately 5 to 12 inches long, and slow burning to provide heat over an extended period. For example, a seven inch long slow burning candle which is approximately one inch in diameter may provide heat for approximately seven hours. Most preferably, the candle 38 is initially seven inches long to, at least initially, locate the flame in the bottom half of the elongated chamber 12. Although the candle 38 can be longer or shorter than seven inches, if the candle 38 is shorter, a single candle heats the entire length of the chamber wall 15 which may cause the chamber 12 to become, too hot, and if the candle 38 is longer, only the upper portion of the chamber 12 is heated, initially decreasing the effectiveness of the heating device 10.

Referring back to FIGS. 1 and 2, the chamber top end 14 is closed with a cap 18 which retains the heat generated by the flame inside the chamber 12. The cap 18 is preferably formed from galvanized steel, and has a collar 50 slidably inserted into the chamber top end 14. The collar 50 has a shape which substantially conforms to the chamber interior shape to provide a snug form fit. The cap collar 50 has holes 54 formed therein, and extends into the chamber 12. Slidably rotating the cap 18 aligns one or more of the collar holes 54 with the chamber vent holes 22 to regulate hot air exiting the chamber 12, and thus the heat retained therein. A rim 52 extend radially from the collar 50 abuts the chamber top end 14 to discourage air from exiting through the chamber top end 14.

The candle 38 may be lit by removing the endcap 24 or inserting a match through a port hole 58 formed in the chamber 12. A flap 56 pivotally mounted over the port hole 58, using a fastener 61, prevents air from entering therethrough once the candle 38 is lit. Advantageously, the flap 56 may be pivoted to increase or decrease the volume of air entering the port hole 56 to control the flame intensity.

A handle 60 attached to the chamber 12, proximal the chamber top end 14, allows the user to carry the heating device 10 without touching the heated chamber 12. The handle 60 is preferably formed from a flexible wire covered with a plastic, insulative coating. Looking particularly at FIG. 2, each end 62 of the handle bare wire pierces the chamber wall 15 and is then knotted. Each knot 64 retains the wire end 62 inside the chamber 12 and prevents the handle 60 from separating therefrom.

To use, the endcap 24 is removed from the chamber 12, and a candle 38 is placed in the candle holder 36. In a preferred method, the candle 38 is lit with a match or other ignition source and then placed inside the chamber 12. Alternatively, the candle 38 is disposed inside the chamber 12 and ignited through the port hole 58 formed in the chamber wall 15.

Once the heating device 10 is generating heat, the entire device is placed between the users clothes and outer wear, such as a roomy jacket or hunting suit. Preferably, the heating device is inserted between the users clothes, and an outer suit which can completely enclose the user when mobility is not required. Using a completely closable suit allows the user to warm the entire body including the users extremities. For example, the user can make any large fabric bag, large enough for the user's body up to waist high, and place the heating device 10 inside the bag with the user, such as between the user's legs, when hunting, such as for deer, duck, and the like, or ice fishing. The device 10 maintains the portion of the body inside the fabric bag warm, and if the user's hands are cold, they can be placed inside the bag for warmth. If the bag is sufficiently large, the bag can enclose the user's entire body for complete body warmth.

The heating device temperature is controlled by twisting the cap 48 to regulate hot air exiting the chamber 12. Twisting the cap 48 in the chamber top end 14 aligns vent holes 22 in the chamber 12 with the holes 54 formed in the cap collar 50. Increasing the number of aligned holes 22, 54 allows a greater volume of air to exit the chamber 12 and reduces the heat retained therein. Decreasing the number of aligned holes 22, 54 retains the hot air inside the chamber 12 and increases the device temperature.

While there has been shown and described what are at present considered the preferred embodiment of the invention, it will be obvious to those skilled in the art that various changes and modifications can be made therein without departing from the scope of the invention defined by the appended claims.

I claim:

1. A personal heating device comprising:

a chamber having a closed end and an open end;

one or more air intake holes formed in said chamber proximal said closed end;

one or more vent holes formed proximal said open end;

a heat source disposed inside said chamber proximal said closed end, wherein heat from said heat source is generated by a flame; and a cap slidably covering said chamber open end;

wherein said chamber closed end is formed by mounting an endcap to said chamber closed end, said endcap having a collar slidably inserted into said chamber closed end, said collar covering one or more air intake holes, wherein said collar being deformed proximal said covered air intake holes such that air enters said chamber through said holes.

2. The heating device as in claim 1, wherein said heat source is a candle.

3. The heating device as in claim 1, wherein said chamber is cylindrical.

4. The heating device as in claim 1, wherein a candle holder is mounted to said endcap.

5. The heating device as in claim 1, wherein said endcap is releasably attached to said chamber.

6. The heating device as in claim 1, wherein said cap has a collar slidably inserted into said chamber open end, said collar having a plurality of holes formed therein, wherein slidably rotating said cap aligns one or more cap collar holes with said vent holes for controlling air venting from said chamber.

7. A personal heating device comprising:

a chamber having a closed end and an open end;

one or more air intake holes formed in said chamber proximal said closed end;

one or more vent holes formed proximal said open end;

a heat source holder disposed inside said chamber proximal said closed chamber end, wherein heat from said heat source is generated by a flame; and a cap slidably covering said chamber open end;

wherein said chamber closed end is formed by mounting an endcap to said closed end, said endcap having a collar slidably inserted into said chamber, said collar covering one or more air intake holes, wherein said collar being deformed proximal said covered air intake holes such that air enters said chamber through said holes.

8. The heating device as in claim 7, wherein said heat source holder is a candle holder.

9. The heating device as in claim 7, further comprising a heat source.

10. The heating device as in claim 7, wherein said heat source is a candle.

11. The heating device as in claim 7, wherein said chamber is cylindrical.

12. The heating device as in claim 7, wherein a candle holder is mounted to said endcap.

13. The heating device as in claim 7, wherein said endcap is releasably attached to said chamber.

14. The heating device as in claim 7, wherein said cap has a collar slidably inserted into said chamber open end, said collar having a plurality of holes formed therein, wherein slidably rotating said cap aligns one or more cap collar holes with said vent holes for controlling air venting from said chamber.

* * * * *